(12) United States Patent
Hill et al.

(10) Patent No.: US 6,656,150 B2
(45) Date of Patent: Dec. 2, 2003

(54) WET/DRY AUTOMATIC INJECTOR ASSEMBLY

(75) Inventors: Robert L. Hill, Abington, MD (US); John G. Wilmot, Mount Airy, MD (US); Steven M Griffiths, Ellicott City, MD (US)

(73) Assignee: Meridian Medical Technologies, Inc., Columbia, MA (US)

( * ) Notice: Subject to any disclaimer, the term of this patent is extended or adjusted under 35 U.S.C. 154(b) by 0 days.

(21) Appl. No.: 09/972,201

(22) Filed: Oct. 9, 2001

(65) Prior Publication Data

US 2002/0049406 A1 Apr. 25, 2002

Related U.S. Application Data

(60) Provisional application No. 60/238,447, filed on Oct. 10, 2000.

(51) Int. Cl.[7] .......................... A61M 37/00; A61M 5/00
(52) U.S. Cl. ........................ 604/89; 604/191; 604/190
(58) Field of Search .......................... 604/82, 89, 191, 604/218, 236, 238, 187, 190, 90–92, 200–202, 87, 88

(56) References Cited

U.S. PATENT DOCUMENTS

| | | | |
|---|---|---|---|
| 4,043,335 A | 8/1977 | Ishikawa | |
| 4,306,554 A | 12/1981 | Schwartz et al. | |
| 4,529,403 A | 7/1985 | Kamstra | |
| 4,599,082 A | 7/1986 | Grimard | |
| 5,569,192 A | * 10/1996 | Van Der Wal | 604/84 |
| 5,704,918 A | 1/1998 | Higashikawa | |

FOREIGN PATENT DOCUMENTS

| | | |
|---|---|---|
| EP | 0 361 668 | 4/1990 |
| EP | 0 405 320 A2 | 1/1991 |
| FR | 2 604 363 | 4/1988 |
| FR | 2 741 810 | 6/1997 |
| WO | WO96/01135 | 1/1996 |
| WO | WO01/93925 | 12/2001 |

OTHER PUBLICATIONS

A copy of the PCT Search Report dated May 3, 2002, issued in the corresponding PCT Application No. PCT/US01/42593.
A copy of the PCT Search Report dated May 3, 2002, issued in related PCT Application No. PCT/US01/42594.
A copy of the PCT Search Report dated May 3, 2002, issued in related PCT Application No. PCT/US01/42595.

* cited by examiner

Primary Examiner—Sharon Kennedy
(74) Attorney, Agent, or Firm—Pillsbury Winthrop LLP

(57) ABSTRACT

The present invention is directed to an automatic injection device containing a pre-loaded charge of medicament for automatically self-administering the medicament upon actuation thereof. The present invention is directed to an automatic injection device containing a pre-loaded charge of medicament for automatically self-administering the medicament upon actuation thereof. The injection device includes a housing assembly, a dry compartment located within the housing for storing a predetermined dry charge of dry medicament therein, and a wet compartment located within the housing for storing a predetermined amount of liquid injection solution therein. The injection device further includes an activation assembly that enables the pressurization of the liquid injection solution in the wet compartment. The activation assembly also enables the compression of the dry medicament within the dry compartment upon activation of the automatic injection device. The activation assembly further facilitates passage of the liquid injection solution from the wet compartment to the dry compartment upon activation of the automatic injection device.

15 Claims, 3 Drawing Sheets

WET/DRY AUTOMATIC INJECTOR ASSEMBLY

CROSS REFERENCE TO RELATED APPLICATION

This application claims priority from U.S. Provisional Ser. No. 60/238,447, filed Oct. 10, 2000, and is incorporated herein in its entirety by reference

FIELD OF THE INVENTION

The present invention relates to automatic injectors for delivering medicament to an injection site. In particular, the present invention is directed to an automatic injector assembly for quickly combining a liquid material with a dry material to form a liquid medicament for delivering the medicament to an injection site. In accordance with the present invention, the automatic injector assembly includes a pair of movable plunger assemblies within the injector assembly for pressurizing the liquid injection solution and compressing the dry medicament.

BACKGROUND OF THE INVENTION

An automatic injector is a device for enabling an individual to self-administer a dosage of medicament into his or her flesh. The medicament is usually stored in liquid form. The advantage of automatic injectors is that they contain a measured dosage of a liquid medicament in a sealed sterile cartridge and can be utilized for delivering the medicament into the flesh during emergency situations. Another advantage of automatic injectors is that the self-administration of the medicament is accomplished without the user initially seeing the hypodermic needle through which the medicament is delivered and without having the user to manually force the needle into his or her own flesh.

There are drawbacks associated with the storage of medicament in liquid form. Some medicaments are not stable in liquid form. Furthermore, some liquid medicaments typically have a shorter shelf life than their solid counterparts. Others have developed automatic injectors that store the medicament in solid form and a liquid injection solution. These injectors, disclosed for example in U.S. Reissue Pat. No. 35,986, entitled "Multiple Chamber Automatic Injector," (the disclosure of which is incorporated herein specifically by reference), however, require the user of the injector to expedite dissolution of the solid component by manually shaking the liquid component and the solid component immediately prior to injection. This increases the time needed to administer a dose of medicament. Furthermore, the improper mixing of the medicament with the liquid injection solution may release an insufficient dose of medicament. There is a need for an automatic injector that stores medicament in solid form that does not require manual premixing by the user. Furthermore, rapid delivery of the medicament is needed for emergency medical situations (e.g. nerve gas and chemical agent poisoning).

OBJECTS OF THE INVENTION

It is therefore an object of the present invention to provide an automatic injector device that stores medicament in a solid form for increased shelf life.

It is another object of the present invention to provide an automatic injector device that automatically mixes a solid medicament with a liquid injection solution upon activation.

It is another object of the present invention to provide an automatic injector device that pressurizes a stored liquid injection solution upon activation of the automatic injector device.

It is another object of the present invention to provide an automatic injector device that compresses the dry medicament upon pressurization of the stored liquid injection solution.

It is another object of the present invention to provide an automatic injector device that minimizes residual space within the injector device to limit the trapping of dry medicament.

It is another object of the present invention to provide an automatic injector device that permits the injection of a medicament without the need for shaking the automatic injector device.

Additional objects and advantages of the invention are set forth, in part, in the description which follows, and, in part, will be apparent to one of ordinary skill in the art from the description and/or practice of the invention.

SUMMARY OF THE INVENTION

In response to the foregoing challenges, applicants have developed an innovative automatic injection device having both wet and dry storage compartments. The present invention is directed to an automatic injection device containing a pre-loaded charge of medicament for automatically self-administering the medicament upon actuation thereof. The present invention is directed to an automatic injection device containing a pre-loaded charge of medicament for automatically self-administering the medicament upon actuation thereof. The injection device includes a housing assembly, a dry compartment located within the housing for storing a predetermined dry charge of dry medicament therein, and a wet compartment located within the housing for storing a predetermined amount of liquid injection solution therein. The injection device further includes an activation assembly that enables the pressurization of the liquid injection solution in the wet compartment. The activation assembly also enables the compression of the dry medicament within the dry compartment upon activation of the automatic injection device. The compression of the medicament occurs independently of the application of pressure on the liquid injection solution. The activation assembly further facilitates passage of the liquid injection solution from the wet compartment to the dry compartment upon activation of the automatic injection device. The injection device also includes a needle assembly for dispensing the liquid injection solution containing the medicament dissolved therein.

In accordance with present invention, it is contemplated that the activation assembly may include a first pressure element that applies pressure to the liquid injection solution within the wet compartment upon activation of the automatic injection device. The activation assembly may further include a second pressure element that compresses the dry medicament within the dry compartment upon activation of the automatic injection device. The second pressure element provides a barrier between the wet compartment and the dry compartment to prevent the transfer of the liquid injection solution from the wet compartment to the dry compartment prior to activation of the automatic injection device.

The activation assembly may further include a linking member for transmitting a force from the first pressure element and the collet to the second pressure element to facilitate compression of the dry medicament. It is contemplated that the first pressure element frictionally engages the linking element to apply a force from the first pressure element to the linking element. The application of pressure on the second pressure element through the linking element occurs such that the dry medicament may be compressed prior to the pressurization of the liquid injection solution. The linking element is slidably received within an aperture within the first pressure element. The linking member is adapted to come in or be in contact with the second pressure element. The linking element may include a stepped surface or have a slight change in diameter on the shaft of the linking member such that the first pressure element contacts the stepped surface/change in diameter to initially drive the second pressure element, which ensures pressure on the dry medicament. The force of the spring assembly may be sufficient to overcome the forces associated with the diameter change of the linking element, whereby the first pressure element slides along the linking element to pressurize the liquid injection solution and force the solution into the dry compartment.

The present invention is also directed to a method of mixing a dry medicament with a liquid injection solution in an automatic injection device for administering a dosage of medicament to a user. The automatic injection device includes a dry compartment for storing the dry medicament prior to mixing, a wet compartment for storing a supply of liquid injection solution prior to mixing, and a needle assembly for transferring a mixture of dissolved dry medicament and the liquid injection solution to a user. The method includes activating the automatic injection device, pressurizing the liquid injection solution in the wet compartment and simultaneously compressing the dry medicament in the dry compartment. The method further includes opening a fluid path between the wet compartment and the dry compartment to permit the passage of the liquid injection solution from the wet compartment to the dry compartment, dissolving the dry medicament in the liquid injection solution within the dry compartment, and transferring the mixture of the dissolved dry medicament and the liquid injection solution through the needle assembly to the user.

In accordance with the present invention, the pressurization of the liquid injection solution in the wet compartment may include applying a force on a first pressure element within the wet compartment. The compression of the dry medicament in the dry compartment may include transferring a force from the first pressure element to a second pressure element, and compressing the dry medicament with the second pressure element. The opening of the fluid path between the wet compartment and the dry compartment may include moving the second pressure element from a first position to permit the passage of the liquid injection solution from the wet compartment to the dry compartment around the second pressure element.

BRIEF DESCRIPTION OF THE DRAWINGS

The invention will be described in conjunction with the following drawings in which like reference numerals designate like elements and wherein.

DETAILED DESCRIPTION OF THE INVENTION

Figure 1:
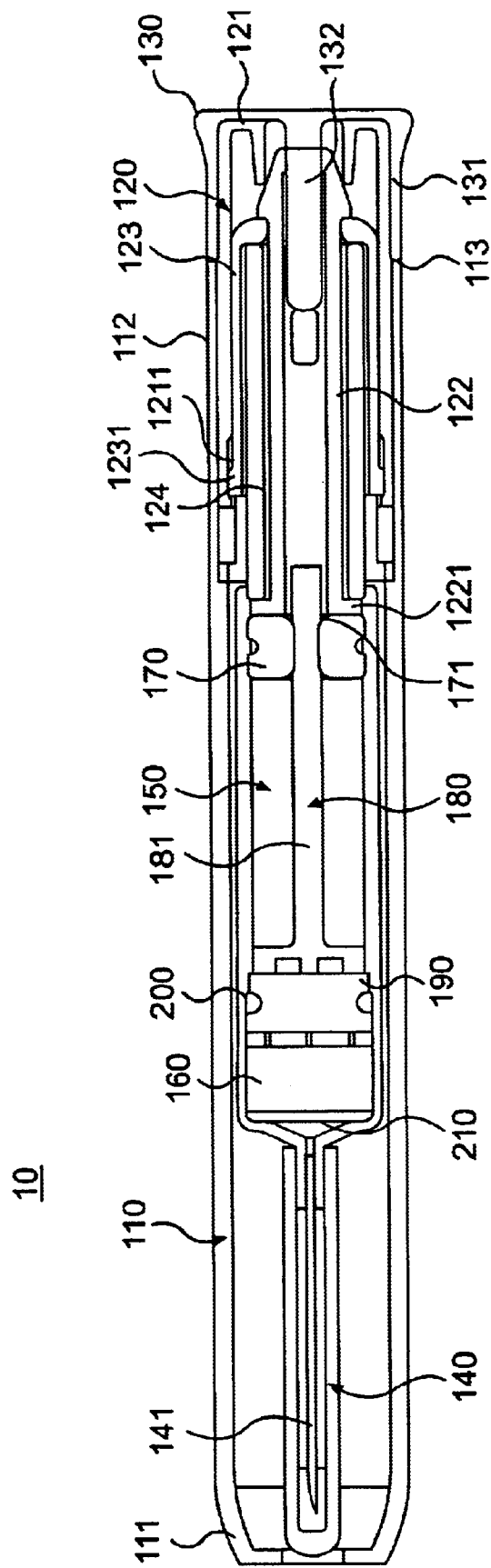
FIG. 1 is a cross-sectional side view of a wet/dry automatic injector assembly in accordance with the present invention.

Referring now, more particularly to the figures, there is shown in FIG. 1 an automatic injector assembly 10. The present invention is described in connection with a push button type auto injector, whereby the user removes an end cap assembly and presses a button to trigger the injection process. The present invention, however, is not limited to push button type automatic injectors; rather, it is contemplated that the present invention may be incorporated into a nose activated auto injector, as described for example in U.S. Pat. No. 5,658,259. The disclosures of which are hereby specifically incorporated herein by reference. It is also contemplated that the present invention may be adapted for use in a syringe or similar article for administering a dosage of medicament. The present invention is directed to an assembly that provides a low residual system with little dead space that may trap liquid and/or medicament.

The automatic injector assembly 10 includes a generally hollow housing 110. The housing 110 includes an injection insertion end 111 and an activation end 112, as shown in FIG. 1. An actuator assembly 120 extends from an opening 113 in the activation end 112 of the housing 110. The actuator assembly 120 is slidably received within the housing 110. A removable end cap assembly 130 is releasably secured to the actuator assembly 120. When the end cap assembly 130 is secured to the actuator assembly 120, a side portion 131 of the end cap assembly 130 is adapted to abut the housing 110 to prevent movement of the actuator assembly 120 and unintentional injection of the medicament.

Figure 2:
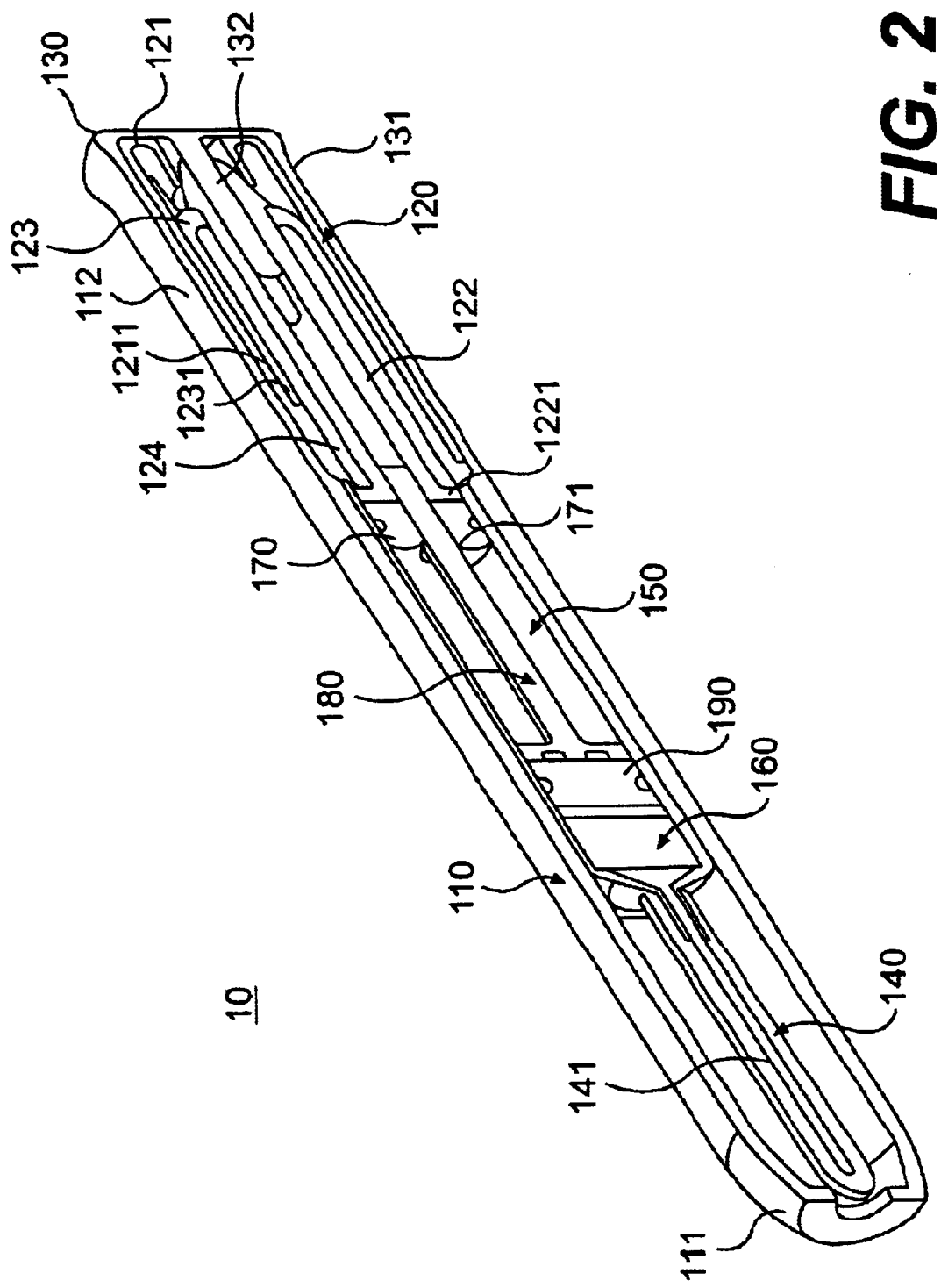
FIG. 2 is a partial cross-sectional schematic view of the wet/dry automatic injector assembly of FIG. 1.

The actuator assembly 120 includes a push button actuator assembly 121 having a hollow interior. The end cap assembly 130 engages the push button actuator assembly 121. A collet 122 is located within the hollow interior of the push button actuator assembly 121. An inner tube 123 is also located within the hollow interior of the push button actuator assembly 121. The inner tube 123 is adapted to contact the collet 122, as shown in FIGS. 1 and 2. An opposite end of the inner tube 123 may include an engagement rib 1231 that is adapted to be received within a complementary recess 1211 within the push button actuator assembly 121. A drive assembly 124 is positioned within a space formed between the collet 122 and the inner tube 123. A pin 132 extends from the end cap assembly 130 and is received within the collet 122 to prevent or block the collet 122 from collapsing prior to activation.

The user removes the end cap assembly 130. The pin 132 no longer prevents movement of the collet 122. Upon depression of the actuator assembly 121, the drive assembly 124 provides the necessary force when activated to operate the injector to inject the user with a necessary dosage of medicament. It is contemplated that the drive assembly 124 may be a spring assembly, a compressed gas assembly or any other suitable energy storing device. When activated, the drive assembly 124 causes the collet 122 to move such that a needle assembly 140 extends from an opening in the injection end 111 of the housing 110. Movement of the collet 122 also causes mixing of the dry medicament with the liquid injection solution, described in greater detail below. Prior to activation, there is no pressure on the dry medicament within the dry container 160.

One end 1221 of the collet 122 extends into a wet container 150 located within the housing 110 for holding the liquid injection solution. The end 1221 of the collet 122 is adapted to contact a first plunger assembly 170 located within the wet container 150. The first plunger assembly 170 is adapted to engage the side wall of the wet container 150 to prevent leakage of the contents (e.g. liquid injection solution) of the wet container 150 from the activation end 112 of the housing 110. The first plunger assembly 170 is preferably formed from a material having low frictional properties such that the collet 122 and first plunger assembly 170 may easily slide within the wet container 150 when operated. Alternatively, the first plunger assembly 170 may be lubricated with silicon or other suitable non reactive lubricant. The movement of the collet 122 and the first plunger assembly 170 pressurizes the liquid located within the wet container 150.

The first plunger assembly 170 includes a central passageway 171 extending therethrough, as shown in FIG. 1. Extending through the central passageway 171 is a lance assembly 180. The lance assembly 180 extends through the wet compartment 150 and is adapted to contact a second plunger assembly 190, which separates the wet compartment 150 from the dry compartment 160. The shaft 181 of the lance assembly 180 is capable of travelling within the collet 122 such that the full volume of liquid within the wet compartment 150 can be delivered to the dry compartment 160. A suitable medicament is located within the dry container 160. It is contemplated that the dry medicament may be in either powder or freeze-dried form. To aid in the mixture of the dry medicament with the liquid injection solution contained in the wet container 150, it is desirable that the medicament be compressed while mixing with the liquid injection solution in the dry container 160. The second plunger assembly 190 prevents mixing of the dry medicament and liquid injection solution prior to activation of the automatic injector assembly.

The second plunger assembly 190 forms a barrier between the wet compartment 150 and the dry compartment 160. The second plunger assembly 190 is adapted to engage the side wall of the wet container 150 to prevent passage of the contents (e.g. liquid injection solution) of the wet container 150 into the dry compartment 160 prior to activation of the automatic injection assembly. The second plunger assembly 190 is preferably formed from a material having low frictional properties such that the second plunger assembly 190 may easily slide when operated. Alternatively, the second plunger assembly 190 may be lubricated with silicon or other suitable non reactive lubricant. The movement of the second plunger assembly 190 compresses the dry medicament located within the dry container 160 and opens a fluid pathway between the wet and dry compartments 150 and 160.

During operation, the spring assembly 124 releases the collet 122, which applies pressure on the first plunger assembly 170. The application of pressure on the first plunger assembly 170 moves the first plunger assembly 170 in the direction of the needle assembly 140. The first plunger assembly 170 engages the lance assembly 180 such that the fist plunger assembly 170 and the second plunger assembly 190 move together until the medicament is compressed. The first plunger assembly 170 through central passageway 171 frictionally engages the lance assembly 180, which causes the lance assembly 180 to also move in the direction of the needle assembly 140. The passageway 171 may engage an increased diameter section or stepped portion on the shaft 181 of the lance assembly 180. Upon contact, the lance assembly 180 moves the second plunger assembly 190 towards the needle assembly 140. This movement of the second plunger assembly 190 compresses the dry medicament located within the dry compartment 160 and opens a fluid passageway 200 between the wet compartment 150 and the dry compartment 160. The first plunger assembly 170 then moves along the shaft 181 of the lance assembly 180 to pressurize and drive the liquid into the dry compartment 160. The fluid passageway 200 may include recesses formed in the sidewall of the wet compartment 150 and the dry compartment 160, which open upon movement of the second plunger assembly 190. It is contemplated that the fluid passageway 200 may be formed by a reduced fit between the wet container 150 and the second plunger assembly 190, a series of by-pass slots, a change in diameter in the compartments, ribs on the container that distort the second plunger assembly or any other assembly that is capable of permitting the flow of liquid injection solution around the second plunger assembly 190.

The movement of the collet 122 under the force of the spring assembly 124 continues to move the first plunger assembly 120 towards the needle assembly 140. As such the liquid injection solution remains under pressure as the volume of the wet compartment 150 decreases through movement of the first plunger assembly 170. As the first plunger assembly 170 moves along the lance assembly 180, the frictional forces between first plunger assembly 170 and the lance assembly 180 continue to act on the lance assembly 180, which applies pressure on the second plunger assembly 190. With this arrangement, the dry medicament within the dry compartment 160 remains under compression. Maintaining the dry medicament under compression during to injection, accelerates the dissolution of the solid medicament into the liquid injection solution. Furthermore, this prevents the liquid injection solution entering the dry container 160 from forming channels within the dry medicament, which would impede dissolution of the medicament within the solution. As such, liquid injection solution containing less than the necessary dosage of medicament may be injected into the user.

In order for the automatic injector assembly to operate effectively, the frictional forces between the second plunger assembly 190 and the side wall of the wet container 150 and the dry container 160 must be less than the frictional forces between the first plunger assembly 170 and the lance assembly 180.

The liquid injection solution mixed with the medicament may then exit the dry compartment 160 through the needle assembly 140 opposite the wet compartment 150. A medicament support assembly 210 may be located adjacent the needle assembly 140 to prevent any undissolved medicament from entering the needle assembly 140. The support 210 may include a filter, it may be a porous material.

As discussed above, the movement of the collet 122 and drive assembly 124 causes the injection needle 141 of the needle assembly 140 to advance and protrude through the housing 110. The injection of the medicament can be performed with a simple operation. The user simply removes the end cap assembly 130, locates the injection end of the housing 110 adjacent the injection site and presses the push button actuator assembly 121. This operation automatically triggers the operation of the drive assembly 124 to advance the collet 122, which advances the first plunger assembly 170, the lance assembly 180, and the second plunger assembly 190 causing the liquid injection solution located within the wet compartment 150 to enter the dry compartment 160. The dissolved medicament is then transmitted through the injection needle 141 to provide the user with the necessary dose of medicament. The automatic injector in accordance with the present invention reduces the amount of time required to administer medicament compared to other wet/dry injectors. The present invention eliminates the need for mixing by the user.

Figure 3:
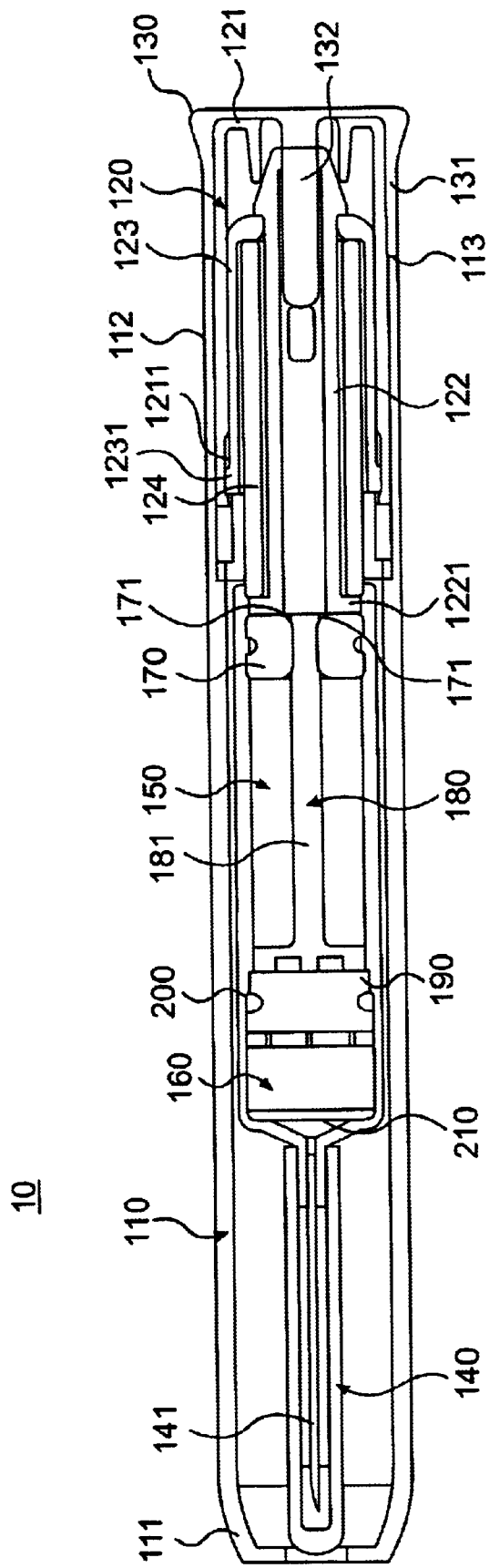
FIG. 3 is a cross sectional side view of a wet/dry automatic injector according to another embodiment of the present invention.

It will be apparent to those skilled in the art that various modifications and variations may be made without departing from the scope of the present invention. For example, it is contemplated that a cover assembly, described for example in U.S. Pat. No. 5,295,965 (the disclosure of which is specifically incorporated herein by reference) may be secured to the injection end of the housing 110 after deployment of the medicament. Furthermore, the automatic injector may further include a nipple plunger assembly, as described for example in U.S. Pat. No. 5,465,727 (the disclosure of which is specifically incorporated herein by reference). It is also contemplated the lance assembly 180 may be connected with the second plunger assembly 190 such that the dry medicament is compressed upon movement of the lance assembly 180. The first plunger assembly 170 may include a membrane 171 that is either applied to the plunger assembly 170 or formed as part of the plunger assembly 170, as shown in FIG. 3. Upon application of force, the shaft 181 of the lance assembly 180 breaks through the membrane 171. This provides an additional barrier that provides better sterility. Thus, it is intended that the present invention covers the modifications and variations of the invention, provided they come within the scope of the appended claims and their equivalents.

What is claimed is:

1. An automatic injection device containing a pre-loaded charge of medicament for automatically self-administering the medicament upon actuation thereof, said automatic injection device comprising:

a housing assembly;

a dry compartment located within the housing for storing a predetermined dry charge of dry medicament therein;

a wet compartment located within the housing for storing a predetermined amount of liquid injection solution therein;

an activation assembly for pressurizing the liquid injection solution in the wet compartment, wherein the activation assembly permits passage of the liquid injection solution from the wet compartment to the dry compartment upon activation of the automatic injection device; and a needle assembly for dispensing the liquid injection solution containing the medicament dissolved therein, wherein the activation assembly includes a drive assembly, whereby upon actuation of the activation assembly, the drive assembly releases a stored source of energy for causing the liquid injection solution in the wet compartment to be transferred to the dry compartment and the liquid injection solution containing the medicament to be dispensed through the needle assembly.

2. The automatic injection device according to claim 1, wherein the activation assembly further compressing the dry medicament within the dry compartment upon activation of the automatic injection device.

3. The automatic injection device according to claim 1, wherein the activation assembly includes a first pressure element that applies pressure to the liquid injection solution within the wet compartment upon activation of the automatic injection device.

4. The automatic injection device according to claim 3, wherein the activation assembly further compressing the dry medicament within the dry compartment upon activation of the automatic injection device.

5. The automatic injection device according to claim 4, wherein the activation assembly includes a second pressure element that compresses the dry medicament within the dry compartment upon activation of the automatic injection device.

6. The automatic injection device according to claim 5, wherein the second pressure element provides a barrier between the wet compartment and the dry compartment to prevent the transfer of the liquid injection solution from the wet compartment to the dry compartment prior to activation of the automatic injection device.

7. The automatic injection device according to claim 5, wherein the activation assembly further includes a linking member for transmitting a force from the first pressure element to the second pressure element.

8. The automatic injection device according to claim 7, wherein the first pressure element selectively engages the linking member.

9. The automatic injection device according to claim 8, wherein the linking member is slidably received within an aperture within the first pressure element.

10. The automatic injection device according to claim 7, wherein the linking member is in contact with the second pressure element.

11. The automatic injection device according to claim 10, wherein the linking member extends through the wet compartment to engage the second pressure element.

12. A method of mixing a dry medicament with a liquid injection solution in an automatic injection device for administering a dosage of medicament to a user, wherein the automatic injection device includes a dry compartment for storing the dry medicament prior to mixing, a wet compartment for storing a supply of liquid injection solution prior to mixing, and a needle assembly for transferring a mixture of dissolved dry medicament and the liquid injection solution to a user, the method comprising:

activating the automatic injection device whereby the following automatically occurs:

pressurizing the liquid injection solution in the wet compartment;

compressing the dry medicament in the dry compartment;

opening a fluid path between the wet compartment and the dry compartment to permit the passage of the liquid injection solution from the wet compartment to the dry compartment;

dissolving the dry medicament in the liquid injection solution within the dry compartment; and transferring the mixture of the dissolved dry medicament and the liquid injection solution through the needle assembly to the user.

13. The method according to claim 12, wherein pressurizing of the liquid injection solution in the wet compartment comprises applying a force on a first pressure element within the wet compartment.

14. The method according to claim 13, wherein compressing the dry medicament in the dry compartment comprises:

transferring a force from the first pressure element to a second pressure element; and compressing the dry medicament with the second pressure element.

15. The method according to claim 14, wherein the opening of the fluid path between the wet compartment and the dry compartment comprises:

moving the second pressure element from a first position to permit the passage of the liquid injection solution from the wet compartment to the dry compartment around the second pressure element.

* * * * *

UNITED STATES PATENT AND TRADEMARK OFFICE
CERTIFICATE OF CORRECTION

PATENT NO. : 6,656,150 B2
DATED : December 2, 2003
INVENTOR(S) : Robert Hill et al.

It is certified that error appears in the above-identified patent and that said Letters Patent is hereby corrected as shown below:

<u>Title page,</u>
Item [73], Assignee, replace "Meridian Medical Technologies, Inc., Columbia, MA (US)" with -- Meridian Medical Technologies, Inc., Columbia, MD (US) --.

Signed and Sealed this

Twenty-third Day of March, 2004

JON W. DUDAS
*Acting Director of the United States Patent and Trademark Office*